(12) United States Patent
Tatischeff et al.

(10) Patent No.: US 7,722,855 B2
(45) Date of Patent: May 25, 2010

(54) EXTRACELLULAR VESICLES FROM NON-PATHOGENIC AMOEBAE USEFUL AS VEHICLE FOR TRANSFERRING A MOLECULE OF INTEREST TO AN EUKARYOTIC CELL

(75) Inventors: Irène Tatischeff, Orsay (FR); Annette Alfsen, Palaiseau (FR); Françoise Lavialle, Antony (FR)

(73) Assignee: Universite Pierre et Marie Curie-Paris VI, Paris (FR)

( * ) Notice: Subject to any disclaimer, the term of this patent is extended or adjusted under 35 U.S.C. 154(b) by 806 days.

(21) Appl. No.: 10/564,284

(22) PCT Filed: Jul. 13, 2004

(86) PCT No.: PCT/IB2004/002265

§ 371 (c)(1),
(2), (4) Date: Mar. 14, 2006

(87) PCT Pub. No.: WO2005/004925

PCT Pub. Date: Jan. 20, 2005

(65) Prior Publication Data

US 2007/0104738 A1    May 10, 2007

(30) Foreign Application Priority Data

Jul. 15, 2003    (EP)    ................................. 03291752

(51) Int. Cl.
*A61K 51/00*    (2006.01)
*A61K 35/68*    (2006.01)
*C12N 1/10*    (2006.01)

(52) U.S. Cl. .................. 424/1.11; 424/9.321; 424/1.21; 424/417; 435/258.1

(58) Field of Classification Search ........................ None
See application file for complete search history.

(56) References Cited

U.S. PATENT DOCUMENTS

2002/0028215 A1    3/2002    Kadurugamuwa et al.

OTHER PUBLICATIONS

Tatischeff et al., CMLS Cellular and Molecular Life Sciences, vol. 54, pp. 475-487, 1998.*
Tatischeff et al., Journal of Fluorescence, vol. 18, pp. 310-328, 2008.*
"The Cellular Slime Molds", John Tyler Bonner, second edition 1967, pp. 34-44.*
Tatischeff I et al: "Dictyostelium discoideum cells shed vesicles with associated DNA and vital stain Hoechst 33342" CMLS Cellular and Molecular Life Sciences, vol. 54, No. 5, May 1998, pp. 476-487, XP002261692 ISSN: 1420-682X cited in the application the whole document.
Kadurugamuwa J L et al: "Delivery of the Non-Membrane-Permeative Antibiotic Gentamicin Into Mammalian Cells by Using Shigella Flexneri Membrane Vesicles" Antimicrobial Agents and Chemotherapy, American Society for Microbiology, Washington, DC, US, vol. 42, No. 6, Jun. 1998, pp. 1476-1483, XP002947117 ISSN: 0066-4804 the whole document.
Arnoult Damien et al: On the evolutionary conservation of the cell death pathway: Mitochondrial release of an adoptosis-inducing factor during Dictyostelium discoideum cell death: Molecular Biology of the Cell, vol. 12, No. 10, Oct. 2001, pp. 3016-3030, XP002261693 ISSN: 1059-1524 p. 3014, left-hand, last paragraph-right-hand column, paragraph 1, p. 3018, right-hand column, paragraph 5 p. 3020, right-hand column, last paragraph.
Francoise Lavialle et al., "Nanovesicles released by Dictyostelium cells: a potential carrier for drug delivery", International Journal of Pharmaceutics, 2009, pp. 206-215, vol. 380, Elsevier B.V.
Claire Wilhelm et al., "Intracellular Trafficking of Magnetic Nanoparticles to Design Multifunctional Biovesicles", Small, 2008, pp. 577-582, vol. 4, No. 5, Wiley-VCH GmbH & Co. KGaA.

* cited by examiner

*Primary Examiner*—Eileen B O Hara
(74) *Attorney, Agent, or Firm*—Young & Thompson (57) ABSTRACT

The invention relates to membrane vesicles from non-pathogenic amoeba, in particular from the amoeba *Dictyostelium discoideum*, containing a molecule of therapeutic interest, to a method of preparing such vesicles and to the use of said vesicles as a vehicle for transferring the molecule therapeutic interest to an eukaryotic mammalian cell.

32 Claims, 3 Drawing Sheets

EXTRACELLULAR VESICLES FROM NON-PATHOGENIC AMOEBAE USEFUL AS VEHICLE FOR TRANSFERRING A MOLECULE OF INTEREST TO AN EUKARYOTIC CELL

The invention relates to membrane vesicles from non-pathogenic amoeba, in particular from *Dictyostelium discoideum* (Dd), containing a molecule of interest, to a method of preparing such vesicles and to the uses of said vesicles as a vehicle for transferring the molecule of interest to an eukaryotic cell.

Different cell processes common to multicellular organisms have been recently shown as dependent on active targeted vesicular traffic, and therefore related to cell membrane dynamics and composition. The synaptic vesicles from the central nervous system, the vesicles called "exosomes" in the immune system, as well as virion budding from infected cells, are all examples of transmission of information pathways from one cell to another. Exosomes have been shown to originate from late endosomes or multi vesicular bodies (MVB) (Kobayashi et al., 1998). The exosome fusion with cells of the immune system induces stimulation of these cells (Kobayashi et al., 2002). The protein composition of these exosomes appears dependent on the cell, with some common components like tetraspan CD63 and CD82, which play an important role in the targeting of exosomes.

The inventors previously showed that cells of *Dictyostelium discoideum* (Dd), an eukaryotic microorganism, when grown in presence of the (A-T) specific DNA stain Hoechst 33342 (HO342), efficiently expel fluorescent material into their culture medium. Indeed, living Dd cells which are highly resistant against xenobiotics, do not evidence vitally stained nuclei, but when these Dd cells are fixed in methanol 70%, their nuclei appear highly fluorescent, due to the permeabilisation of the nuclear membrane and further staining of the nuclei by the remaining cell-associated HO342 (Tatischeff et al., 1998). Electron microscopy and lipid analysis demonstrated the vesicular nature of the externalised fluorescent material and the presence of HO342 associated with these vesicles was confirmed by fluorescence spectroscopy. It was also shown that living Dd cells release vesicles into their external medium, both during growth and during starvation (Tatischeff et al., 1998; Tatischeff et al., 2001).

The inventors postulated that externalised Dd vesicles may participate in intercellular communication between Dd cells. To gain insight into Dd vesicles function, vesicles were prepared either from the growth medium of Dd cells grown in presence of HO342, or from the starvation medium of the same cells starved during 22 h in buffer without HO342. HO342, a bis benzimidazole positively charged hydrophobic molecule that is an (A-T) specific DNA stain, exhibits fluorescence characteristics which are dependent on its environment and association state. These characteristics have been used to follow the state of HO342 inside Dd vesicles. The inventors have demonstrated the capacity of the dye-containing vesicles to mediate the transfer of the fluorescent dye to nuclei of naive living Dd cells, and more importantly to efficiently target the dye to the nuclei of human cells, either multidrug sensitive or resistant. Interestingly, the transfer efficiency of HO342 to the cells by Dd vesicles was found to be improved compared with liposomes containing the dye. These results identify Dd vesicles as mediators of intercellular communication.

Since other amoebae have been shown to shed extracellular vesicles, these results further indicate that non-pathogenic amoeba vesicles are useful as a new vehicle for the transport of a molecule of interest, in particular a therapeutic molecule, to eukaryotic cells, such as mammalian cells. Furthermore, these vesicles have a plasma membrane which composition is close to that of mammalian cells and deprived of virulence factors. This lack of pathogenic character makes it possible for a safe use of the vesicles, while avoiding side effects such as septic shock that may be encountered with vesicles originating from other microorganisms, such as bacteria. Thus the vesicles according to the invention may find applications in vaccination, gene therapy, or any other therapeutic or prophylactic treatment where the transfer of a molecule of interest to a eukaryotic cell may be required.

DEFINITIONS

As used herein, the term "non-pathogenic amoeba" denotes a protozoan belonging to the amoeba class, which is not pathogenic for a living eukaryotic cell or a living organism. Examples of non-pathogenic amoeba include for instance *Dictyostelium* amoebae, such as *Dictyostelium discoideum*, or amoebae from the genus *Acanthamoeba*, such as *Acanthamoeba royreba*, or from the genus *Entamoeba*, such as *Entamoeba histolytica*. Preferably the non-pathogenic amoeba according to the invention is *Dictyostelium discoideum*.

"*Dictyostelium discoideum*", also called "*D. discoideum*" or "Dd", is a non-pathogenic soil-living protozoan that grows as separate, independent cells. Upon exposure to adverse conditions, for instance starvation, *D. discoideum* amoebae interact by chemotaxis, through cAMP release and relay, to form multicellular structures, and aggregate to form a mound that is surrounded by an extracellular matrix. *D. discoideum* cells comprise or display many features characteristic of higher eukaryotic cells, e.g. cytokinesis, motility, phagocytosis, chemotaxis, signal transduction, as well as processes of developmental biology, such as cell sorting, pattern formation, and cell-type determination. In growing conditions, the amoeba remains as an undifferentiated cell and multiplies by mitosis. Further severe starvation, *D. discoideum* cells aggregate into multicellular mounds and differentiate into two main cell types.

As used herein, the term "non-pathogenic amoeba vesicles" is meant for extracellular vesicles that are shed from non-pathogenic amoeba cells. In particular, "*D. discoideum* vesicles" denotes extracellular round-shaped vesicles, as may be observed by electron microscopy, that are released by living Dd cells into their external medium, during growth or starvation. The size of these vesicles is generally less than 500 nm; it preferably ranges from about 50 nm to about 500 nm, still preferably between 100 and 300 nm. Said vesicles are composed of a lipid bilayer containing a cytosolic fraction. *D. discoideum* vesicles lipid bilayer contains usual phospholipids (phosphatidylcholine (PC), phosphatidic acid (PA), phosphatidylethanolamine (PE), phosphatidylinositol (PI), phosphatidylserine (PS), phosphatidylglycerol (PG), diphosphatidylglycerol (DPG)), sphingomyelin (Sph), as well as the lysophospholipid lyso bis phosphatidic acid (LBPA).

The term "molecule of interest" is meant for any molecule, such as a therapeutic molecule, or a label molecule, for which the transfer to a eukaryotic cell may be desired. Additionally, said molecule of interest may be an imaging agent useful in medical diagnosis, such as a magnetic resonance imaging contrast agent, an ultrasound imaging agent, or a nuclear imaging agent. Preferably the molecule of interest is exogenous to the non-pathogenic amoeba. The term "exogenous" as used herein is synonymous of "heterologous", i.e. it refers to a molecule that is not naturally found in the non-pathogenic amoeba vesicles, or to a molecule that is not expressed by growing non-pathogenic amoeba cells. Said molecule may be a peptide, polypeptide, protein, nucleic acid (DNA or RNA oligonucleotides or polynucleotides), lipid, or more generally any chemical, biological, or synthetic molecule. Preferably, depending on the object of the invention, said molecule of interest is not Hoechst 33342 (also called HO342). The molecule of interest may be carried on (i.e. in the membrane) or within (i.e. in the lumen) the vesicles of the invention.

In the context of the invention, "therapeutic molecule" refers to any active molecule capable of reversing, alleviating, inhibiting the progress of, or preventing a pathologic disorder or condition, or a symptom of said disorder or condition. Therapeutic molecules may include a small therapeutic protein/peptide (interleukins, growth factors, chemokines), an hormone, a protein such as an enzyme or a receptor, a nucleic acid such as an oligodeoxynucleotide, or a DNA (in particular in the form of a DNA plasmid) or RNA encoding a pharmacological peptide or protein as well as an antisense nucleic acid, ribozyme, or <<small interfering RNAs" (siRNAs) that blocks translation of a specific mRNA. Therapeutic molecules more generally include any biological, chemical, or synthetic molecule known to achieve a therapeutic effect in vitro and/or in vivo, such as chemotherapeutic agents for the treatment of cancers, infections, etc. . . .

The term "transfer" as used herein, refers to the introduction of the molecule of interest into cells.

As used herein the term "eukaryotic cell" denotes a cell which has a chromosome-containing nucleus surrounded by its proper membrane, which isolates the nucleus from the cytoplasm. This term applies to a cell from any (eukaryotic) unicellular microorganism, fungi, as well as to plants, animals and humans. Preferably said eukaryotic cell is heterologous to the non-pathogenic amoeba, in particular said cell is a mammalian cell, e.g. a human, mouse, sheep, or monkey cell. Still preferably, said mammalian cell, in particular human cell, is, naturally or induced, multidrug resistant.

"Pharmaceutically" or "pharmaceutically acceptable" refer to molecular entities and compositions that do not produce an adverse, allergic or other untoward reaction when administered to an animal, or a human, as appropriate.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

Non-Pathogenic Amoeba Vesicles Preparation

The invention provides a method for preparing vesicular vehicles useful for transferring one or more molecules of interest to an eukaryotic cell, which vehicles is a non-pathogenic amoeba vesicle, preferably *Dictyostelium discoideum* vesicle, containing said molecules of interest.

The invention thus relates to a method for preparing a non-pathogenic amoeba vesicle containing a molecule of interest, which method comprises the steps consisting of:
  a) culturing a non-pathogenic amoeba cell in a culture medium comprising said molecule of interest, under conditions sufficient to allow the non-pathogenic amoeba cell to release vesicles;
  b) recovering a vesicle released by said cell, which vesicle contains said molecule of interest.

Preferably said molecule of interest is exogenous to the non-pathogenic amoeba. Also preferably said molecule of interest is not Hoechst 33342.

As the vesicles of the present invention can be used to deliver a broad range of pharmaceutical compositions and drugs, the molecule of interest is preferably a nucleic acid, a small organic or inorganic compound such as bioactive agents. Examples of pharmaceutical or bioactive agents include, but are not limited to, antimicrobial agents, antibiotics, antimycobacterial, antifungal, or antiviral agents, agents affecting the immune response, blood calcium regulators, agents useful in glucose regulation, anticoagulants, antithrombotics, antihyperlipidemic agents, cardiac drugs, thyromimetic and antithyroid drugs, adrenergics, antihypertensive agents, cholinergics, anticholinergics, antispasmodics, antiulcer agents, skeletal and smooth muscle relaxants, prostaglandins, general inhibitors of the allergic response, antihistamines, local anesthetics, analgesics, narcotic antagonists, antitussives, sedative-hypnotic agents, anticonvulsants, antipsychotics, anti-anxiety agents, antidepressant agents, anorexigenics, non-steroidal anti-inflammatory agents, steroidal anti-inflammatory agents, antioxidants, vaso-active agents, bone-active agents, anti-arthritics agents and antineoplastic agents.

In particular, the molecule of interest may be an antineoplastic agent, such as vincristine, doxorubicin, hypericin, mitoxantrone, camptothecin, cisplatin, bleomycin, cyclophosphamide, methotrexate, streptozotocin, and the like.

The molecule of interest may also be an imaging or diagnostic agent to be targeted, for instance, to a neoplastic tissue. In particular, the diagnostic agent may be an imaging agent for tracking progression of a disease. Imaging agents include for instance chelate of radionuclides, such as technetium-99, or iodine-125.

According to a first embodiment, the extracellular vesicles are directly recovered from a culture medium in which non-pathogenic amoeba cells were grown in the presence of the molecule of interest. Said vesicles may be recovered for instance after reaching late (or end of) exponential growth phase.

According to a second embodiment, non-pathogenic amoeba cells may be cultured and grown, for instance up to late (or end of) exponential growth phase, in a first culture medium appropriate to sustain cell growth and in the presence of the molecule of interest. Non-pathogenic amoeba cells may then be transferred in a second culture medium, optionally in the presence of the molecule of interest, under conditions sufficient for the non-pathogenic amoeba cells to release extracellular vesicles. In particular, said second culture medium may be totally deprived of the nutrients required to sustain cell growth ("starvation medium"). The non-pathogenic amoeba vesicles are then recovered from said second "starvation" culture medium.

Suitable conditions for culturing non-pathogenic amoebae are known to the one of ordinary skill in the art.

Advantageously, the non-pathogenic amoeba according to the invention is *Dictyostelium discoideum*. *D. discoideum* vesicles are naturally released from *D. discoideum* cells with no need to expose said cells to a stress stimulus, such as a chemical stress or a thermal stress, for instance. Furthermore it is acknowledged in the art that *D. discoideum* cells are particularly easy to grow. The amoebae grow on bacterial lawns or in liquid cultures of semi-defined or completely defined media with doubling times of 3 to 12 hours. Over $10^{10}$ *D. discoideum* cells can be grown in a few days without sophisticated equipment. Above this amount of cells, growth in bioreactors is required and has already been experimented (Poppenborg et al. (1997)). Appropriate culture conditions thus may be readily defined by the one skilled in the art. Such conditions may comprise for instance growing cells in suspension in a culture medium, for instance HL5 semi-defined medium, containing a suitable carbon source, such as yeast extract, as described by Sussman (1987) or Watts and Ashworth (1970). The culturing of D. discoideum cells is more thoroughly detailed in the following examples. The culture period may be variable, for instance ranging from 24 to 96 hours, preferably from 48 to 72 hours. Duration of the culture may be readily adjusted by the one skilled in the art depending on the number of cells inoculated in the culture medium and on the amount of vesicles to be collected.

The invention advantageously makes use of the high resistance to xenobiotics displayed by D. discoideum cells. Actually D. discoideum cells exposed to a molecule of interest, in particular an exogenous molecule, have the capacity to uptake said molecule and to expel it into the culture medium via the vesicles released into the extracellular space. D. discoideum vesicles can encapsulate large quantities of interest molecules, such as therapeutic molecules, either within their aqueous interiors or dissolved into the hydrocarbon regions of their lipid bilayers.

The molecule of interest may be added to the cultured cells, preferably when initiating growth or during exponential growing phase. The concentration of the molecule of interest in the culture medium may be adjusted by the one skilled in the art so that said molecule does not exhibit toxicity towards the non-pathogenic amoeba cells. The one skilled in the art may readily determine suitable concentrations by routine experiment, for instance by comparing the growth rate or proliferation of non-pathogenic amoeba cells cultured in the presence or not of the molecule of interest. Importantly, the inventors found that the concentration of the molecule of interest in the lumen of the vesicles is correlated with the concentration of the molecule of interest in the culture medium. The method of the invention thus makes it possible to modulate the concentration of the molecule of interest encapsulated within the vesicles by adjusting the concentration of said molecule in the culture medium.

The non-pathogenic amoeba vesicles are separated from non-pathogenic amoeba cells, isolated from the culture medium, and optionally concentrated. To that end, the cultured cells may be removed by centrifugation (for instance at 700 g for 5 minutes) and the resulting supernatant may then be cleared by another centrifugation step (for instance 2,000 g for 10 minutes). The vesicle may be pelleted by 12,000 g and 105,000 g ultracentrifugation. However, the recovery of the extracellular vesicles should not be limited to this embodiment and it will be understood that any appropriate means enabling to isolate the vesicles is within the scope of the invention. Mention may be made for instance of ultrafiltration, nanofiltration, biomagnetic separation and chromatography, such as size exclusion chromatography, affinity chromatography, etc . . . .

The vesicles so obtained may be stored for several weeks at 4° C. They are very stable and can resist several freezing/thawing cycles in liquid nitrogen.

Non-Pathogenic Amoeba Cells and Vesicles

The invention further relates to a non-pathogenic amoeba cell, in particular a D. discoideum cell, which has been cultured in the presence of a molecule of interest and to the extracellular vesicles obtainable by a method as described above.

More specifically, the vesicle according to the invention is a vesicle from a non-pathogenic amoeba that contains a molecule of interest, with the proviso that said vesicle is not a D. discoideum vesicle containing Hoechst 33342. Preferably said vesicle is a vesicle from D. discoideum. Also preferably, said molecule of interest is exogenous to the non-pathogenic amoeba.

The inventors demonstrated that D. discoideum vesicles efficiently transferred HO342 to multidrug resistant human cells. Since HO342 is a known substrate of Pgp, a protein involved in cell multidrug resistance, this finding supports that D. discoideum vesicles, and more generally non-pathogenic amoeba vesicles, constitute a vehicle useful for the delivery of therapeutic molecules to cells, in particular those that display multidrug resistance.

Thus, preferably said molecule of interest may be a therapeutic molecule, such as an antitumoral agent. Antitumoral agents may be chemotherapeutic drugs that initiate cytotoxicity through interactions with a variety of molecular targets. Chemotherapeutic drugs include for instance topoisomerase inhibitors, alkylating agents that form adducts with the nucleophilic centers of DNA and proteins, platinum compounds, pyrimidine and purine antimetabolites, or microtubule targeting drugs. Most cancer drugs induce cell death, at least partially, via downstream events leading to programmed cell death or apoptosis. Furthermore said antitumoral agent may be a cytokine, capable of enhancing the immune response elicited by a tumor antigen and thus stimulate the host's defense against a tumor. Said molecule may also be a small Mr compound, such as an antitumoral drug or the Differentiation Inducing Factor (DIF) from D. discoideum that is structurally related to the antitumoral drug differanisole A.

De novo and acquired cross-resistance to multiple antitumoral agents can result from several alternative factors and processes. However, multidrug resistance (MDR) patterns are frequently associated with decreased drug accumulation, usually due to increased drug efflux, principally mediated by ABC transporters like the P-glycoprotein (MDR1, P-170) or the more recently identified multidrug resistance protein (MRP, P-180) family members. Another multidrug resistance-related protein, the lung resistance protein (LRP), was identified as a "vault" protein by comparison with protein sequence of Dictyostelium (Izquierdo et al., 1996). Hereafter, these proteins and encoding genes are altogether called "MDR" proteins and genes, respectively. Accordingly, a therapeutic molecule according to the invention may further be a molecule silencing a MDR protein expression or by-passing the MDR protein. As already mentioned this approach may for instance utilize antisense nucleic acids or ribozymes that block translation of a specific mRNA, either by masking this mRNA with an antisense nucleic acid or cleaving it with a ribozyme. For a general discussion of anti-sense technology, see, e.g., Antisense DNA and RNA, (Cold Spring Harbor Laboratory, D. Melton, ed., 1988). Reversible short inhibition of MDR gene transcription may also be useful. Such inhibition can be achieved by use of siRNAs. RNA interference (RNAi) technology prevents the expression of genes by using small RNA molecules such as <<small interfering RNAs" (siRNAs). This technology in turn takes advantage of the fact that RNAi is a natural biological mechanism for silencing genes in most cells of many living organisms, from plants to insects to mammals (Sharp, 2001). RNAi would prevent a gene from producing a functional protein by ensuring that the molecule intermediate, the messenger RNA copy of the gene is destroyed. siRNAs could be used in a naked form and incorporated in a vesicle according to the invention.

However, other therapeutic molecules are contemplated and the invention should not be limited to the field of cancer therapy. Among the potential therapeutic molecules, mention may be made of molecules useful for the treatment of an infection, in particular a bacterial, viral or parasitic infection. These molecules may be an antigenic peptide, an antibody, an antibiotic, an anti-viral agent such as interferon, an anti-protease agent, etc . . . . For instance, where the vesicle according to the invention is to be used for vaccination purposes, the molecule of interest may be advantageously an antigenic peptide associated with an adjuvant such as a lipopolysaccharide (LPS), Freund's adjuvant, or any other adjuvant known in the art. Furthermore, the vesicles of the invention may be used to vehicle Immunoglobulins A (IgA) to intestinal epithelial cells so as to achieve mucosal vaccination.

Additionally, the MDR silencing strategy disclosed above may further find application in the context of mucoviscidose treatment. Actually the efficacy of the chemotherapeutic treatment of mucoviscidose, which is intended for the treatment and prevention of bacterial infection of the obstructed bronchi, may be jeopardize by the onset of drug resistance upon drug administration. Therefore, non-pathogenic amoeba vesicles containing means (antisense, siRNA, etc . . . ) for silencing the expression of the transporter(s) responsible for drug resistance or chemical compounds able to bypass the drug resistance proteins could prove useful for enhancing mucoviscidose treatment efficacy.

Non-Pathogenic Amoeba Vesicles as Delivery Vehicles and Uses Thereof

The above non-pathogenic amoeba vesicles comprise vehicles useful for delivering of a molecule of interest to a target cell. Once taken up by a target cell, non-pathogenic amoeba vesicles facilitate the cytoplasmic and/or the nucleus delivery of an encapsulated molecule of interest, such as a therapeutic molecule, by fusing with the endosomal and/or nucleus membranes.

Furthermore, as demonstrated in the following examples, the non-pathogenic amoeba *D. discoideum* vesicles proved to be more efficient than liposomes in the transfer of HO342 to living *D. discoideum* cells. Without willing to be linked to a particular theory, it is thought that this improved transfer efficiency may be due to the closest composition of *D. discoideum* vesicle lipid bilayer with cell cytoplasmic and endosomal membranes. This similarity would make it easier for non-pathogenic amoeba vesicles, and in particular *D. discoideum* vesicles, to fuse with cell membranes and thus deliver the material contained in its interior or lipid bilayer.

Accordingly, the invention further relates to a vehicle useful for in vitro and/or in vivo transferring a molecule of interest to a eukaryotic cell, in particular a mammalian cell, which vehicle consists in, or comprises, a *D. discoideum* vesicle as described above. Said vehicle may consist in or comprise a *D. discoideum* vesicle that contains Hoechst 33342.

The invention also relates to the use of a non-pathogenic amoeba vesicle containing a molecule of interest, as described above, including a *D. discoideum* vesicle that contains Hoechst 33342, as a vehicle useful for in vitro, ex vivo and/or in vivo transferring a molecule of interest to an eukaryotic cell, in particular a mammalian cell.

Preferably said non-pathogenic amoeba is *D. discoideum*.

Accordingly a method for in vitro and/or ex vivo transferring a molecule of interest to an eukaryotic cell is provided, which method comprises the step consisting of contacting an eukaryotic cell with a vehicle according to the invention, i.e. a non-pathogenic amoeba vesicle containing a molecule of interest, including a *D. discoideum* vesicle that contains Hoechst 33342, under conditions sufficient to allow the non-pathogenic amoeba vesicle to fuse with the eukaryotic cell, whereby the molecule of interest is transferred to the eukaryotic cell. Such contact may be carried out for instance by culturing said eukaryotic cell in the presence of non-pathogenic amoeba vesicles. Preferably, said molecule of interest is exogenous to the non-pathogenic amoeba. Preferably said non-pathogenic amoeba is *Dictyostelium discoideum*.

A method for in vivo transferring a molecule of interest to an eukaryotic cell is further provided, which method comprises the step consisting of contacting an eukaryotic cell with a vehicle according to the invention, i.e. a non-pathogenic amoeba vesicle containing a molecule of interest, including a *D. discoideum* vesicle that contains Hoechst 33342, under conditions sufficient to allow the non-pathogenic amoeba vesicle to fuse with the eukaryotic cell, whereby the molecule of interest is transferred to the eukaryotic cell. More specifically said method may comprise administering a mammal with a non-pathogenic amoeba vesicle containing a molecule of interest, under conditions suitable to allow the non-pathogenic amoeba vesicle to fuse with a cell of said mammal, whereby the molecule of interest is transferred to said cell. Preferably, said molecule of interest is exogenous to the non-pathogenic amoeba. Preferably said non-pathogenic amoeba is *Dictyostelium discoideum*.

The non-pathogenic amoeba vesicle may be administered for instance according to any suitable route usually used in the art where a liposome or other membrane vesicle delivery means is to be administered. For instance topical, oral, parenteral, intranasal, intravenous, intramuscular, subcutaneous or intraocular administration and the like may be contemplated.

The non-pathogenic amoeba vesicle according to the invention can be administered either alone or in the form of a composition, in mixture with a physiologically-acceptable carrier (such as physiological saline or phosphate buffer) selected in accordance with the route of administration and standard pharmaceutical practice. The composition may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc. Additionally, the composition may include lipid-protective agents which protect lipids against free-radical and lipid-peroxidative damages on storage. Lipophilic free-radical quenchers, such as a-tocopherol and water-soluble iron-specific chelators, such as ferrioxamine, are suitable.

Thus, a pharmaceutical composition comprising a non-pathogenic amoeba vesicle, in particular a *D. discoideum* vesicle, containing a therapeutic molecule together with a pharmaceutically acceptable carrier is within the scope of the invention. Actually using these non-pathogenic amoeba vesicles, the invention provides a method for the treatment of diseases that can be improved by administering a therapeutically effective amount of the non-pathogenic amoeba vesicles containing the therapeutic molecule. These may be for instance diseases characterized by aberrant expression of a gene in a mammalian subject, including tumors. Said therapeutic molecule may be in particular an antisense nucleic acid component that hybridizes specifically with the aberrantly expressed gene. As used herein the term "therapeutically effective amount" means an amount which provides a therapeutic benefit. For antisense oligonucleotide this means generally 0.5 to 50 mg/kg of body weight, but when delivered in a lipid particle formulation, a below-toxic amount of lipids must be used.

Preferably said vesicles may be utilized for the therapy of pathological disorders wherein a multidrug resistance phenotype may arise, such as cancer, mucoviscidose etc . . . . Furthermore, said vesicles may also be used to supplement a defective mutated gene.

The application will be further understood in view of the following figures and examples.

EXAMPLES

Example 1

Materials and Methods

*Dictyostelium* Cells

Growth and Vital Staining by HO342

Dd cells, cloned Ax-2 strain, were grown in suspension in HL5 semi-defined medium (Sussman, 1987; Watts and Ashworth., 1970), on a gyratory shaker (150 rpm) at 22° C. For proper oxygenation, each suspension was grown in an Erlenmeyer holding five times the suspension volume with addition of antibiotics (Biomedia) (penicillin (50 U/ml), streptomycin (50 U/ml)). Dd cells are able to grow and divide at the expense of soluble or particulate nutrients to produce vegetative cells, which were generally used in the late exponential phase of growth for starvation.

In the present work, cells were grown as above (control) or in the presence of HO342 (Molecular Probes). HO342 stock solution (≈1 mg/ml) was prepared in de-ionized water, filter sterilized (0.22 µm), stored at −20° C., and diluted to the appropriate concentration (4-44 µg/ml) when initiating the culture with HO342. For most experiments, cells were incubated with HO342 during 24 h. In some experiments, cells were incubated with HO342 (10 µg/ml) for periods of time ranging from 24 h to 216 h. Cells, grown with HO342 or without, were used further for preparation of vesicles, and, sometimes, for starvation before preparation of vesicles, without any HO342 added during starvation.

Starvation

To initiate cell starvation, cells at the end of their exponential growth—with or without HO342—were harvested by centrifugation at 700 g for 5 min, washed twice in ice-cold potassium phosphate buffer (17 mM, pH 6.8) (buffer A), and resuspended in this buffer at a density of $4 \times 10^7$ cells/ml at time 0 ($t_0$). Cells were starved 22 h on a gyratory shaker (150 rpm) at 22° C., in proper oxygenation conditions.

Cell Fixation

In a few experiments, Dd cells grown in presence of HO342 were prepared as described for starvation, but resuspended at a density of $2 \times 10^7$ cells/ml in cold (−20° C.) methanol:buffer A (70:30 v/v). Fixation was achieved after 10 min at −20° C. and cells were kept at 4° C. until use.

Preparation of Vesicles

At the end of the time of growth of the cells with HO342 or after the same time for the cells grown without HO342, cells were harvested and both growth media were prepared cell-free by centrifugation at 700 g for 5 min and kept at 4° C. The $t_{22}$ starvation media were prepared in the same way. For preparation of vesicles, each medium was clarified by centrifugation at 2,000 g for 10 min (4° C.), giving rise to a supernatant S/2,000. <<12,000>> vesicles were prepared from S/2,000 by centrifugation at 12,000 g for 20 min (4° C.). <<105,000>> vesicles were obtained from S/12,000 by centrifugation at 105,000 g for 45 min (4° C.). Pellets P/12,000 and P/105,000 were resuspended and (×50) concentrated in 40 mM Tris-HCl, pH 7.4, 250 mM sucrose, 5 mM dithiothreitol, 2 mM EDTA (buffer B) and anti-proteases. All chemical reagents were from Sigma. The vesicles were respectively named A1 when prepared from growth medium with HO342 and C1 without HO342 (control). Vesicles prepared from $t_{22}$ starvation media were respectively named A2 (HO342) and C2 (control).

All vesicles, when stored at 4° C., were highly stable and could be kept up to 6 weeks until use.

Human Leukemic K562 Cell Lines

The erythroleukemia K562 cells (ATCC CCL-243), were maintained in suspension in a 25 $cm^2$ (Corning) flask for tissue culture, using RPMI 1640 medium supplemented with 10% fetal calf serum (Biomedia), glutamine (2 mM) and antibiotics (Biomedia) (penicillin (50 U/ml), streptomycin (50 U/ml)). Cells were grown in a 5% $CO_2$ and 95% humidified air atmosphere, at 37° C. The resistant K562r cell line, expressing the multidrug P-glycoprotein, was selected from the normal sensitive K562s cell line as described (Loetchutinat et al., 2003). In order to maintain P-glycoprotein expression, the medium of K562r cells was supplemented with 60 ng/ml colchicine.

For the experiments, K562 cells were harvested at a density about $10^6$ cells/ml. After cell counting on a Buirker hemocytometer, cells were centrifuged (5 min, 300 g) and resuspended at a density of $10^7$ cells/ml in RPMI 1640 medium with 10% fetal calf serum.

SDS-PAGE

After quantification of protein concentrations of Dd vesicles by the method of Peterson (Peterson et al., 1977), SDS-PAGE (8% or 12%) was performed according to Laemmli (1970). SYPRO-red (Molecular Probes) staining (sensitivity similar to silver staining) was used to visualize electrophoretic patterns.

Preparation of Liposomes

Egg phosphatidylcholine and cholesterol (Sigma) have been used for preparation of large unilamellar vesicles (LUV) and small unilamellar vesicles (SUV), according to Olson (Olson et al., 1979).

Video Light-Microscopy

The morphological changes of the growing and/or aggregating Dd cells were controlled by phase contrast microscopy with an Olympus BHA transmission microscope (Scop, Rungis, France) and by low magnification stereomicroscopy (Olympus STZ). UV fluorescence microscopy was performed with the same BHA Olympus microscope, equipped with a 100 W mercury lamp and an ultraviolet-blue fluorescence excitation block.

Images of cells incubated with Dd vesicles were recorded by video light-microscopy with the same BHA microscope. The video set-up was self-made with the following additional components: a C adaptator on the BHA microscope (Olympus, Rungis, France) a Black & White analogic CCD camera and a Black & White video monitor (Optophotonics, Eaubonne, France), a Dazzle Hollywood DV-Bridge for analogic-digital conversion (New Edge, Boulogne Billancourt, France) and an Apple iMac G3 with a FireWire input (Computer Bench, Villejuif, France). Data acquisition was achieved through NIH Image 1.62.

HO342 transfer from Dd vesicles to its intracellular target, i.e. nuclei of living Dd or K562 cells, was observed as follows: 10 µl of cells ($\approx 10^7$ cells/ml, either directly harvested for Dd cells or after concentration by centrifugation for K562 cells) and 10 µl of concentrated Dd vesicles were deposited on a microscope slide under a 20×20 mm cover glass and observed by UV fluorescence video microscopy as a function of time. For overnight observations, cover glasses were sealed on microscope slides with nail varnish to prevent sample evaporation.

Electron Microscopy

Whole mounts of Dd vesicles were observed by negative staining electron microscopy. Pellets obtained after 12,000 g or 105,000 g centrifugation were loaded 30 s on formvar coated nickel grids. Grids were stained 10 s with a droplet of 0.2% (w/v) aqueous uranyl acetate and dried. The grids were observed with a Philips CM12 electron microscope at an accelerating voltage of 80 kV.

Absorption Spectroscopy

Absorption spectra were recorded on a UV-Visible Varian DMS 70 spectrophotometer. Before preparing dilute solutions of HO342 stock solution ($\approx 1$ mg/ml), the concentration was checked by a 1/20 dilution in buffer A. Absorbance measurement was performed in a 2×10 mm quartz cuvet (l=2 mm), using a molar absorbance of $\epsilon=42,000 M^{-1}.cm^{-1}$ at 340 nm. Concentrations are usually given in µg/ml (Mr=616).

Fluorescence Spectrofluorimetry

Steady state fluorescence emission and excitation spectra were obtained on a spectrofluorimeter with an experimental set-up as described in Klein et al., 1987), but automated with a Macilci computer and a Labview software for the acquisition of data. Kaleidagraph was used for the treatment of data. Quartz cuvets of 3×3 mm were positioned with two perpendicular micrometers. The slit widths were 2 and 2 mm for the excitation monochromator (McPherson) and 2 and 1.8 mm for the emission monochromator (Baush & Lomb). All fluorescence measurements were made at 22° C.

For photophysical studies, dilutions of HO342 stock solution were made in buffer A. The interaction between HO342 and DNA was studied by adding HO342 (14.3 µM, final concentration) in buffer A to DNA (33 µM in base pairs, Mr=610, final concentration). The [bp]/[dye] ratio was ~2. *Clostridium perfringens* (Cp) DNA (Sigma) was chosen for its (AFT) base composition similar to the one of Dd DNA. Interaction with lipids was studied by incorporating HO342 (100 µg/ml, initial concentration in buffer A) into LUV, followed by PD-10 column filtration, and further sonication of the LUV fraction to prepare HO342-containing SUV. As a control, SUV were also prepared without the dye and HO342 (40 µg/ml, final concentration in buffer A) was added to the SUV preparation. Interaction with an anionic detergent was followed spectrofluorometrically by adding sodium dodecyl sulfate (SDS) at a final concentration of 2%, i.e. above critical micelle concentration (cmc=8.1 mM), to HO342 in the concentration range of 4-44 µg/ml in buffer A. In some experiments, SDS 2% was added to DNA-bound HO342 and lipid-bound HO342. The (uncorrected) spectra were recorded from 360 to 720 nm, using a 350 nm excitation wavelength. The sample absorbance at this excitation wavelength was usually less than 0.1 in order to eliminate inner filter effects.

Example 2

Morphological Characteristics of Vesicles Expelled by Dd Cells into the Extracellular Media during Growth and Starvation Dd extracellular vesicles (Tatischeff et al., 1998; Tatischeff et al., 2001) have been further purified from growth medium of vegetative ($t_0$) cells and from $t_{22}$ conditioned medium, as detailed in Materials and methods. The different purified A1 and A2 vesicles, as well as C1 vesicles (control vesicles), have been analyzed by negative staining electron microscopy. Whether they contained HO342 or not, most of the vesicles exhibited a round-shaped structure, limited by a lipid-like bilayer membrane. However, the <<105,000>> A2 vesicles exhibited numerous ovoid structures. In the control <<12,000>> C1 preparation, some electron-dense fibrillar structures could be observed beside the vesicles. The vesicle size was heterogeneous, ranging from 57 nm to 500 nm in diameter.

Some interesting details of the vesicle preparations were observed with a higher magnification. <<12,000>> A1 and A2 vesicles depicted varying size. The smaller round-shaped vesicles contained an electron-dense material, excentered near the membrane, whereas the largest ones appeared empty with a folded-up membrane. Among the <<105,000>> A1 and A2 vesicles, the most remarkable features were the appearance of crescent-shaped structures and ovoid structures with a folded-up membrane. Control <<12,000>> and <<105,000>> C1 vesicles appeared mainly homogenously round and less electron-dense, as empty. Some vesicles were characterised by a rather large membrane invagination.

Example 3

Biochemical Analysis of Dd Vesicles

Vesicles prepared and concentrated (×50) from growth media (A1, C1) were first analyzed for their protein content. Table 1 indicates that in control conditions, i.e in the absence of HO342 during growth, a much larger amount of proteins was present in <<105,000>> C1 vesicles as compared to the one in <<12,000>>C1 vesicles. In contrast, protein content of <<12,000>> A1 vesicles purified from growth medium of cells grown with HO342 was significantly higher than that of <<105,000>>A1 vesicles prepared in the same experimental conditions.

TABLE 1

Protein content of *Dictyostelium* A1 and C1 vesicles

| Dd Vesicles | | Protein content ($\mu g/10^8$ cells) |
|---|---|---|
| C1 control | << 12,000 >> | 66 |
| | << 105,000 >> | 110 |
| A1 (HO342) | << 12,000 >> | 141 |
| | << 105,000 >> | 104 |

SDS-PAGE (12%) analysis performed under reducing conditions shows that both <<12,000>> and <<105,000>> C1 vesicles exhibited qualitatively comparable electrophoretic patterns with polypeptides of 97, 66-60, 45, and 30-35 kDa. However, differences in signal intensities were observed for the 66-60 and 45 kDa polypeptides between the <<12,000>> and <<105,000>> (higher and lower intensity for the <<12,000>> C1 vesicles 60 and 45 kDa polypeptides, respectively, compared with the <<105,000>> C1 vesicles). When using gels 8% in acrylamide, a strong signal was detected at 205 kDa with both samples, in agreement with our previous data (Tatischeff et al., 1998). The <<12,000>> and <<105,000>> A1 vesicles, externalised by cells grown with HO342, exhibited electrophoretic patterns qualitatively similar to those observed for the control C1 vesicles.

Example 3

Fluorescence Emission Spectra of HO342 in Buffer and Associated with DNA, Lipids and/or Anionic Detergent SDS In order to analyse the presence of HO342 in Dd vesicles and its possible association state, the fluorescence characteristics of HO342 was first studied, either free in buffer A or associated with DNA, lipids and/or detergent.

Figure 1:
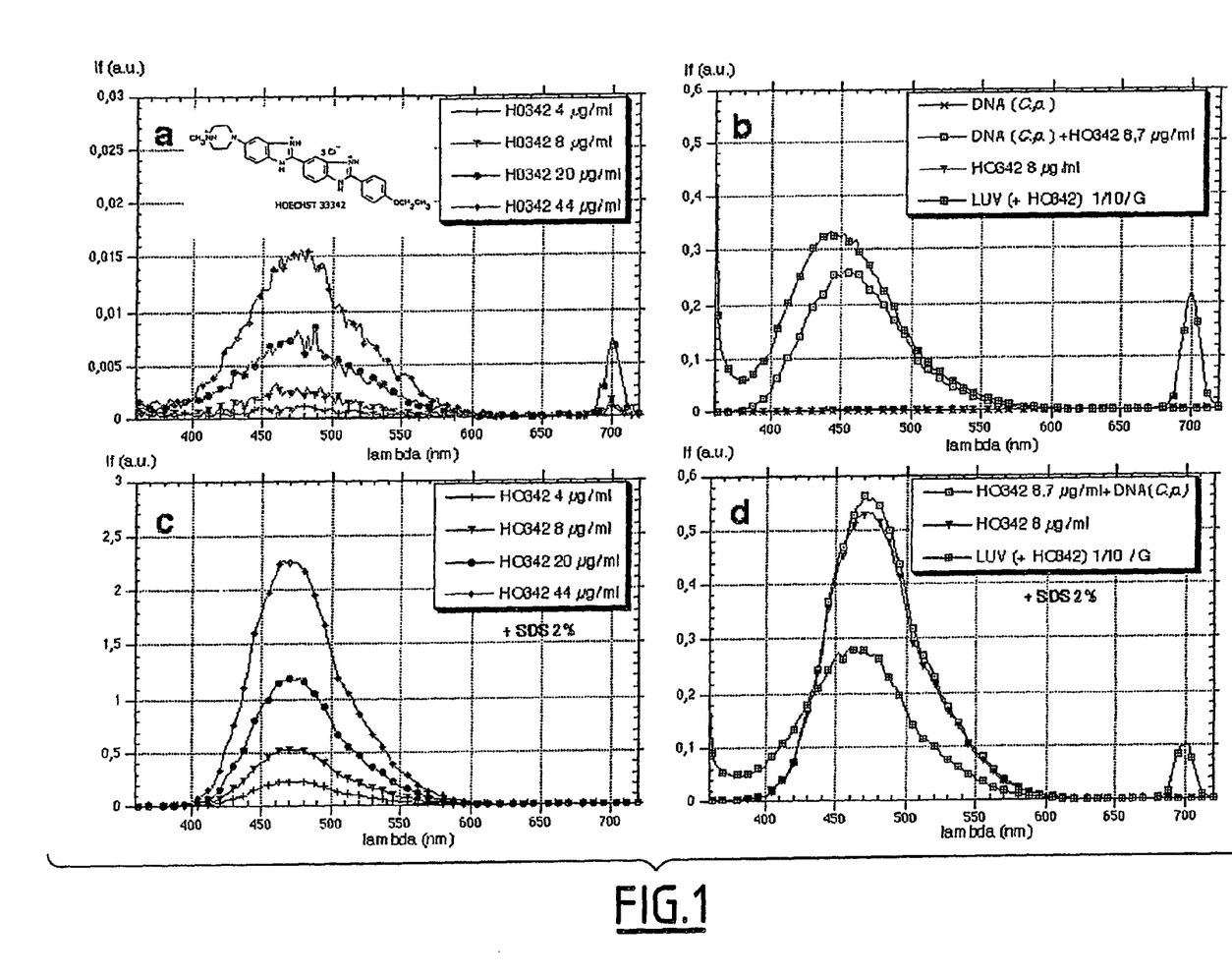
FIG. 1 is a representation of fluorescence emission spectra analysis of Hoechst 33342 excited at 350 nm, free or complexed with DNA, lipids and SDS detergent. (a) The emission peak at 475 nm was of very low intensity (a.u.) for free HO342 (4-44 µg/ml in buffer A). (b) For HO342 (8 µg/ml) added to (Cp) DNA at a [bp]/[dye] ratio ≈2, the emission peak at 450 nm was of a much higher intensity (×100). HO342 associated with large unilaminar vesicles ("LUV"), accounting for the higher second order diffusion at 700 nm, exhibited the same spectral characteristics. (c) In presence of SDS 2%, the emission spectra of HO342 (4-44 µg/ml), peaked at 470 nm, but the intensity was much higher (×170) than the one of free HO342 in buffer A. (d) SDS 2% added to DNA-HO342 or lipid-HO342 complexes (as in b) was compared to SDS 2% added to HO342 8 µg/ml in buffer A. All emission spectra peaked around 470 nm but there was no intensity increase for lipid-HO342 and only an increase ≈2 for DNA-HO342, compared to a factor of 170 for free HO342.

A solution of HO342, in the concentration range 4-44 µg/ml in buffer A, showed a very weak fluorescence emission, linear as a function of concentration, with a maximum wavelength at 475 nm when excited at a wavelength of 350 nm (FIG. 1a). When interacting with (Cp) DNA, at a low [bp]/[dye] ratio ($\approx$2), HO342 exhibited a higher fluorescence intensity (×100) with a blue-shifted emission peak at 452 nm (FIG. 1b), as previously described (Gorner et al., 2001; Cosa et al., 2001).

Interaction of HO342 with lipids was studied by encapsulating the dye into liposomes. In the HO342-containing SUV, an increase in fluorescence intensity and a blue-shifted emission peak at 447 nm were observed (FIG. 1b). Interaction of HO342 with lipids has been mentioned before, but without any spectral characteristics (Shapiro et al., 1995; Shapiro et al., 1997). SDS, an anionic detergent, was also known to interact with HO342, mainly above its cmc of 8.1 mM (Gorner et al., 2001). Indeed, a very high increase was observed for HO342 fluorescence intensity (×170) in the presence of SDS 2% (final concentration in buffer A, highly above cmc) (FIGS. 1a, c), with the same 350 nm excitation wavelength. The emission maximum was at 470 nm instead of 475 nm for free HO342, i.e. with a very small blue shift. Addition of SDS 2% to HO342 interacting with DNA induced a much smaller increase in fluorescence intensity (×2.5) (FIG. 1d), but the emission peaked also at 470 nm, which represents an important red-shift from 452 nm. A comparable spectral behaviour was observed with SDS 2% added to HO342-containing liposomes, i.e. a significant shift from 447 to 470 nm of the emission peak, but without any increase in fluorescence intensity (FIG. 1d). These data indicate that there is a competition between SDS and DNA or lipids for the binding of HO342.

Example 4

Fluorescence Emission Spectra of HO342 in Dd Extracellular Vesicles

Figure 2:
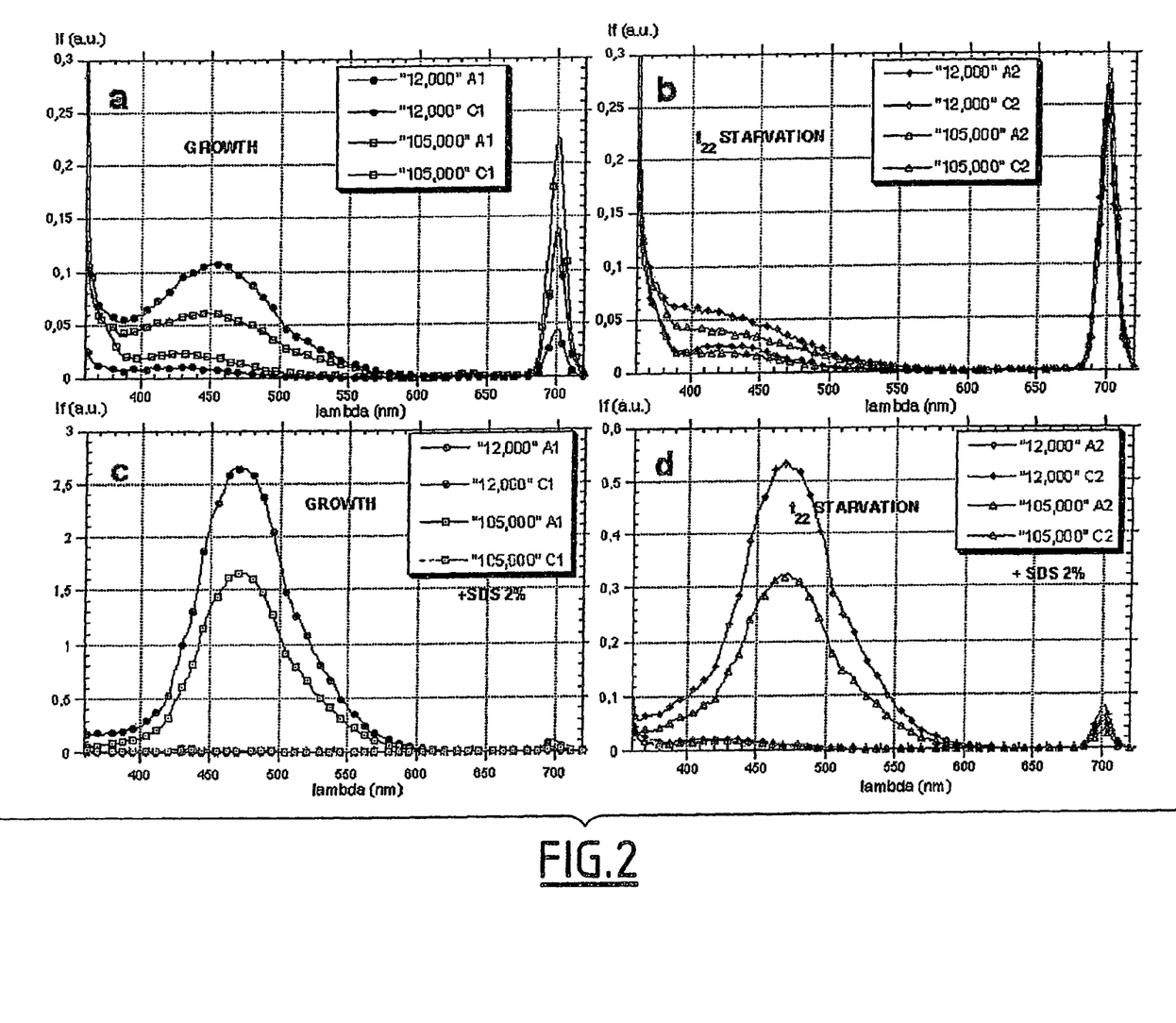
FIG. 2 depicts the fluorescence emission spectra of *Dictyostelium* extracellular vesicles. (a) Emission spectra of <<12,000>> and <<105,000>> A1 Dd vesicles compared to the spectra of the corresponding C1 vesicles, excited at 350 nm: both A1 spectra, of very weak intensity, peaked at 452 nm, whereas C1 spectra showed only a fluorescence background between 400 nm and 500 nm. All second order diffusion peaks at 700 nm were relatively high. (b) Emission spectra of <<12,000>> and <<105,000>> A2 Dd vesicles compared to the spectra of the corresponding C2 vesicles, excited at 350 nm: the high diffusion peaks at 350 nm mask the low intensity emission spectra. (c) Emission spectra of A1 and C1 Dd vesicles as in (a), after addition of SDS (2% final concentration): for both the <<12,000>> and <<105,000>> A1 vesicles, the fluorescence maximum shifted towards 470 nm and the intensity was increased by a factor of ≈25 (note that the scale for $I_f$ in (c) is 10× the scale in (a). In contrast, the spectra of the C1 vesicles were not modified by addition of SDS. (d) Emission spectra of A2 and C2 Dd vesicles as in (b), after addition of SDS (2% final concentration). For both the <<12,000>> and <<105,000>> A2 vesicles, the fluorescence maximum shifted towards 470 nm and the intensity was increased by a factor of ≈10 (the scale for $I_f$ in (d) is 2× the scale in (b). The second order diffusion peaks at 700 nm were largely decreased. The fluorescence spectra of the C2 vesicles were not modified by the addition of SDS, but the decrease of the diffusion peaks was also observed.

The <<12,000>> and <<105,000>> A1 and C1 vesicles were studied by spectrofluorimetry. Both <<12,000>> and <<105,000>>A1 vesicles, excited at 350 nm, exhibited weak intensity emission spectra between 360 and 720 nm (FIG. 2a), with a wavelength maximum around 450 nm, near to the one observed for HO342-DNA or HO342-lipid complexes. The emission spectra of <<12,000>> and <<105,000>> A2 vesicles, when excited at 350 nm, were of lower intensity (FIG. 2b). With the control C1 and C2 vesicles, only a very small background fluorescence was observed between 390 and 500 nm (FIGS. 2a, b). It is worth noting the relatively large second order diffusion component at 700 nm (FIGS. 2a, b), related to the vesicular nature of the materials.

To assess the state of HO342 inside Dd vesicles, SDS 2% has been added to disrupt the vesicle membrane. In all types of vesicles, the detergent effect of SDS was clearly shown by the large decrease of the second order diffusion peak at 700 nm (FIGS. 2c, d).

The HO342 contained in the A1 and A2 vesicles exhibited, in presence of SDS 2%, a fluorescence emission peak at 470 nm (FIGS. 2c, d). Furthermore, the intensity was increased by a factor ≈25 (+/−3) for HO342 in the <<12,000>> and <<105,000>> A1 vesicles and by a factor ≈10 (+/−0.5) for HO342 in the <<12,000>> and <<105,000>> A2 vesicles. As shown previously, the fluorescence of HO342 in interaction with SDS 2% was characterized by a much higher intensity (FIG. 1c) as compared to free HO342 (FIG. 1a). When SDS 2% was added either to HO342-DNA or -lipid complexes, a shift of the maximum wavelength around 450 nm towards the same 470 nm wavelength was observed, but with no important intensity changes (FIGS. 1b, d). The intensity increase observed by disrupting the vesicle membranes by SDS 2%, as compared to the fluorescence characteristics of HO342 in different states of association (FIG. 1) suggests that HO342 contained in Dd vesicles could be partly associated with DNA or/and lipids and partly free inside the vesicles. In contrast, no effect of SDS 2% was observed on the fluorescence spectra of the <<12,000>> and <<105,000>> C1 and C2 vesicles, indicating that the fluorescence characteristics of Dd vesicles are related to their HO342 content.

Example 5

Influence on the Vesicular Externalisation of HO342 of the Dye Concentration in the Cell Growth Medium and of the Incubation Time with Dd Cells The following experiments give an insight of the absence of cytotoxicity of HO342 during incubation with Dd cells in the growth medium and of the efficiency of its vesicular externalisation as a function of the used experimental conditions. The growth curve of Dd cells, continuously maintained with HO342 (10 μg/ml) since the initiation of the culture at a density of $3 \times 10^6$ cells/ml is shown on FIG. 3a. Images of Dd cells, fixed in 70% MeOH at different times (from 72 h to 216 h), show the aspect of the cells and of their HO342 stained nuclei. Apoptosis might increase as a function of time along the stationary plateau (Tatischeff et al., 2001), and the characteristic much smaller size of apoptotic cells were predominant for the $t'_{216}$ fixed Dd cells (FIG. 3a).

Concentrated (×20) <<12,000>> A1 vesicles were prepared after different times of incubation (24 h-165 h) and studied by fluorescence spectroscopy, both with and without addition of SDS 2%, as previously described. The fluorescence of HO342 associated with the vesicles, excited at 350 nm, was increasing from 24 h to 72 h (FIG. 3b), when Dd cells reached the stationary phase of growth (FIG. 3a). A suspension ($5 \times 10^6$ cells/ml in buffer A) of $t'_{95}$ fixed Dd cells (FIG. 3a) exhibited fluorescence spectra with or without SDS 2%, characteristic of HO342-DNA complexes (FIG. 3c). The corresponding fluorescence emission spectra of the concentrated (×20) <<12,000>> A1 vesicles released by these $t'_{95}$ cells (FIG. 3b) exhibited the same maximum at 450 nm, shifted to 470 nm in presence of SDS. However, the observed increase in fluorescence intensity due to interaction with SDS, was ≈11 for the vesicles and only 2.3 for the HO342 stained nuclei in fixed cells. This value is to be compared with the (×2.5) increase in fluorescence intensity observed by adding SDS 2% to the HO342-(Cp) DNA complex (FIGS. 1b, d).

Figure 3:
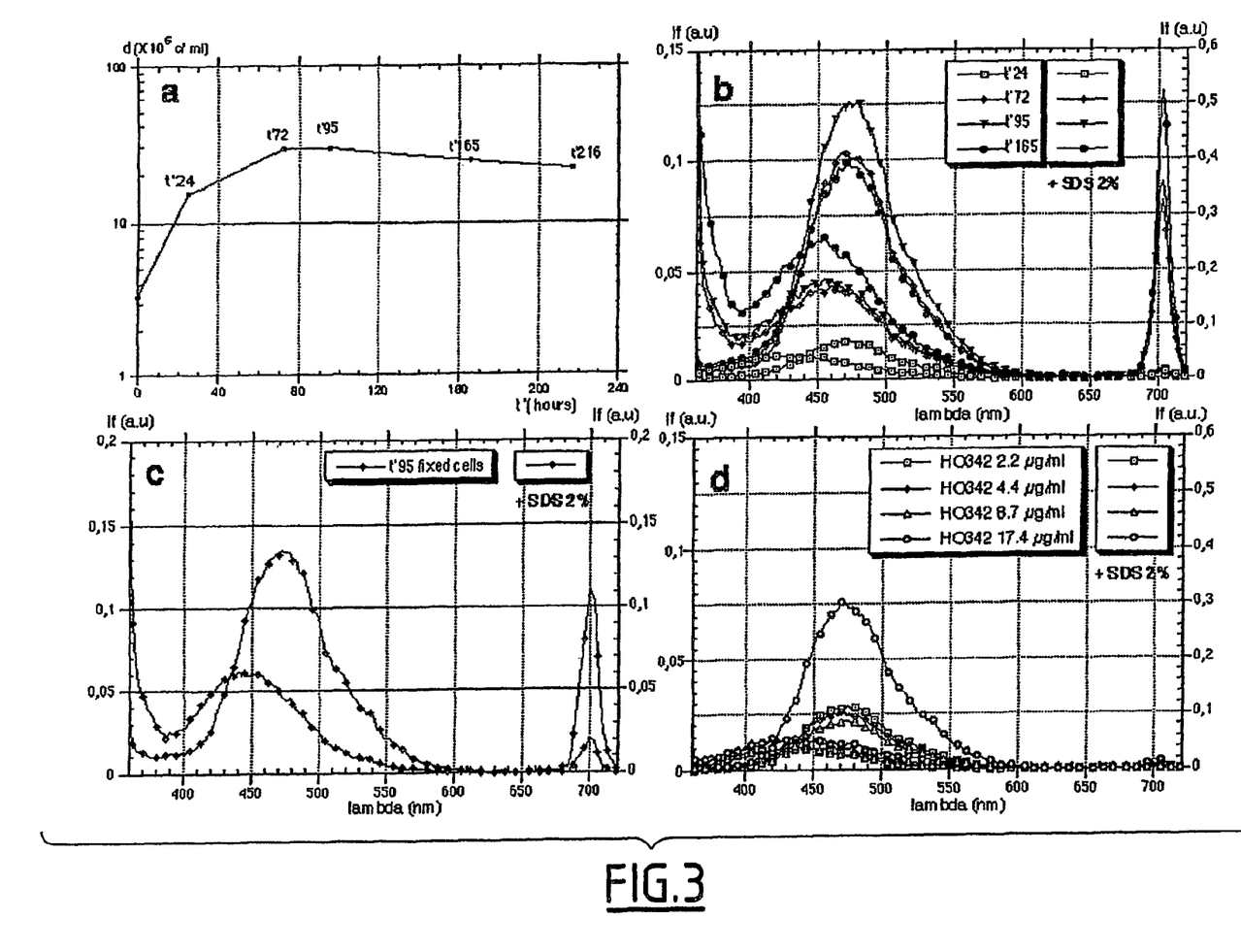
FIG. 3 represents fluorescence emission spectra of <<12,000>> A1 Dd extracellular vesicles as a function of Hoechst 33342 concentration and incubation time with *Dictyostelium* cells during growth. (a) Growth curve of Dd cells, continuously maintained with HO342 (10 µg/ml) since initiation of the culture at a density of $3 \times 10^6$ cells/ml. Images of Dd cells, fixed in 70% MeOH as a function of time (72 h-216 h), show the aspect of the cells and of their HO342 stained nuclei along the stationary plateau. (b) Emission spectra of concentrated (×20) "12,000" A1 vesicles prepared at different time (24 h-165 h) from growth media corresponding to (a). Emission spectra excited at 350 nm are shown with addition of SDS 2% and without, as described in FIG. 2 (note the double Y scale). (c) Emission spectra, excited at 350 nm, of a suspension ($5 \times 10^6$ cells/ml in buffer A) of $t'_{95}$ fixed Dd cells in (a) are shown with addition of SDS 2% and without, for comparison with the corresponding emission spectra of the $t'_{95}$ <<12,000>>A1 vesicles in (b). (d) Emission spectra obtained in the same conditions as in (b) for concentrated (×20) <<12,000>> A1 vesicles, purified from different culture media of Dd cells grown in parallel during 24 h in presence of increasing HO342 concentrations (2.2-17.4 µg/ml, final concentration).

The influence of HO342 concentration (2.2-17.4 μg/ml, final concentration) in the growth media is shown on FIG. 3d. The fluorescence emission spectra of the <<12,000>> A1 vesicles, purified from different growth media of Dd cell cultures, initiated at the same density ($3 \times 10^6$ cells/ml) and grown in parallel during 24 h in presence of increasing HO342 concentrations, did not exhibit any significant variation. However, SDS (2%) disruption of the vesicles originating from Dd cells incubated at the highest HO342 concentration showed the presence of a higher amount of free HO342. In this case, the observed increase in fluorescence intensity due to interaction with SDS, was ≈20, to be compared with an increase ≈10 for the other HO342 concentrations. When comparing the spectra shown on FIGS. 3b and d, the amount of vesicles released in the extracellular medium, as measured by the 700 nm second order peaks, appeared more important only after 72 h of incubation with HO342, i.e. at the stationary phase of growth.

Example 6

Dd A1 Vesicles Mediate the Transfer of HO342 to the Nuclei of Living Dd Cells

The nuclei of Dd cells grown without HO342 became highly stained with the dye, after about ½ h of incubation with Dd concentrated (×50) <<12,000>> A1 vesicles. Three different fields were observed by light microscopy at different times after starting the incubation, either with white light to control the cell appearance, or under UV exciting light for fluorescence observation of the nuclei. After 6 min, very few fluorescent structures appeared, but after 34 min and 67 min almost all of the nuclei were heavily stained within the living cells. As a control, Dd cells were also incubated with the cell growth medium used for the preparation of the A1 vesicles and containing the vesicles before concentration by centrifugation. After 55 min, only a multinucleated Dd cell, having lost its membrane refringency, exhibited nuclei staining. This first observation shows that concentrated (×50) <<12,000>> A1 vesicles are efficient to mediate HO342 transfer to the nuclei of living Dd cells grown without HO342. By contrast, when the HO342-containing SUV studied by spectrofluorimetry (FIG. 1b) were incubated ≈1 h with Dd cells, in the same conditions, no staining of the nuclei was observed.

Dd <<105,000>> A1 vesicles, although containing less HO342 than the <<12,000>> A1 vesicles, as shown by fluorescence spectroscopy (FIGS. 2a, c), were also able to mediate HO342 transfer towards the nuclei of Dd cells. One single field showing a few normal Dd cells and one larger cell, was observed as a function of time of incubation with concentrated (×50) <<105,000>>A1 vesicles. A faint labelling of the nuclei by HO342 in the mono- or binucleated cells appeared only after about 2 h of incubation and full labelling of the nuclei in the multinucleated Dd cell was not achieved before 3 h 36, that is later than with the <<12,000>> A1 vesicles. Observation of the same field by phase contrast microscopy at the beginning (5 min) and at the end (3 h 51) of the UV observations showed a modification of the living cells, but without any features of cell necrosis during such a long time for the cells maintained under a coverslip without proper oxygenation. This suggests a possible protective effect of Dd vesicles against cell stress processes, as compared to cells incubated in the same conditions without concentrated vesicles.

Example 7

Dd A1 Vesicles Mediate the Transfer of HO342 to the Nuclei of Living Human Leukemic K562 Cells, Either Multidrug Resistant or Sensitive Human leukemic K562 cells, sensitive (s) or multidrug resistant (r) (Loetchutinat et al., 2003) were incubated with Dd concentrated vesicles, in order to control the ability of these vesicles to transfer HO342 to nuclei of other living cells than Dd cells. With the concentrated (×50) <<105,000>> A1 vesicles, at a comparable time scale as the one used with Dd cells, the much larger nuclei of the K562r cells became visible by UV fluorescence. Some of the cells had a quite normal appearance after staying ≈4 h under a coverglass, whereas other cells depicted some blebs; however, the cells were still refringent by phase contrast microscopy and their stained nuclei were clearly inside the cells, as observed by simultaneous observation with white light and UV microscopy.

Comparative observations of K562r and K562s cells incubated overnight with less concentrated (×20) <<12,000>> A1 vesicles were carried out. Nuclei were again heavily stained with HO342 but seemed to occupy almost the whole cells, when compared with K562r cells observed for a shorter incubation time. This reduction in cell size might be related to the initiation of an apoptotic process for K562r cells remaining such a long time without proper oxygenation.

The Dd concentrated (×25) <<12,000>> and <<105,000>> A2 vesicles, obtained from $t_{22}$ starved cells, were also able to mediate HO342 transfer to nuclei of K562s cells during an overnight incubation. The nuclei of the K562r cells were also stained by overnight incubation with the Dd concentrated (×25) <<12,000>> A2 vesicles. They were but poorly stained with the Dd <<105,000>> A2 vesicles.

After overnight incubation with Dd concentrated (×25) <<12,000>> A2 vesicles and <<105,000>> A2 vesicles, the much smaller Dd nuclei were also stained with HO342 inside Dd cells.

This study by video light-microscopy shows that Dd externalised vesicles are able to interact with other living cells targeting their HO342 content into the nuclei of either Dd cells or human leukemic K562 cells, and this, independently of the huge differences in size of their nuclei and genomes. Dd vesicles containing HO342 or not appeared to protect the cells against necrosis linked to a lack of oxygenation during about 4 h. However, an overnight incubation was probably too long and did induce some apoptotic morphological changes, such as a reduction in cell size and cell blebbing, specially for the K562r cells.

Example 8

D. discoideum Vesicles Constitute an Efficient Delivery Vehicle for Transfer of Exogenous Molecules to Human Cells The above results demonstrated that *D. discoideum* vesicles containing HO342 efficiently target the dye to the nuclei of human K562 cells, either multidrug sensitive or resistant.

Leukemic K562 cells were previously found (Asahi et al., 1995) to differentiate and recover the capacity to synthesize haemoglobin upon exposure to a *D. discoideum* differentiation inducing factor (DIF, Morris et al., 1987). DIF is a small molecular weight molecule that shows structural analogy with the antitumoral compound differanisole A.

Accordingly *D. discoideum* cells are grown in the presence of DIF so as to encapsulate the differentiation factor within the extracellular vesicles. It is worth noting that growing *D. discoideum* cells do not synthesize DIF, which thus can be regarded as an exogenous molecule to *D. discoideum* cells during growth phase.

Said vesicles are further isolated and concentrated and further contacted with K562 cells, as described above with the vesicles containing HO342, so as to assess whether K562 cells acquired capacity to synthesize haemoglobin, i.e. whether the differentiated phenotype of the K562 cells is reverted by DIF-containing Dd vesicles.

The present data show that the cells of the unicellular eukaryotic microorganism *D. discoideum* externalise vesicles containing endogenous and exogenous molecules. Dd cells can be grown or starved in rather large suspensions, therefore allowing easy isolation from the growth or starvation medium of large amount of these vesicles.

Purification of the vesicles, either externalised from cells grown in presence or not of the vital DNA stain HO342, or expelled by the same cells after a 22 h starvation period in buffer A, led to isolate different types of vesicles. They were separated in two groups by ultracentrifugation at 12,000 g and 105,000 g.

Electron microscopy studies and biochemical analyses evidenced the vesicular nature of the material, as well as some characteristics in common with the vesicles secreted by some mammalian cells and named "exosomes" (Denzer et al., 2000a; Kobayashi et al., 2002). Electron microscopy of the different types of purified Dd vesicles, studied by negative staining at high magnification, gave indication of similarities with the electron microscopy of exosomes originating from the MVBs of many mammalian cells (Kobayashi et al., 1998; Denzer et al., 2000a; Blanchard et al., 2002). To confirm such similarities, it would be necessary to control, by immunoelectron microscopy, the presence on Dd vesicles of some specific markers of mammalian exosomes, namely the tetraspan proteins CD82 and CD63, which are suggested to play a role in their cell targeting (Denzer et al., 2000a).

The protein analysis of Dd vesicles indicated the presence of polypeptides of 97, 66-60, 45, and 30-35 kDa. This has to be compared with the proteins associated with the purified Dd endocytic vesicles (Rodriguez-Paris et al., 1993; Nolta et al, 1994, Adessi et al., 1995). Among the major proteins, identified by sequence analysis, attention has to be paid, beside actin and a Rab 7-like GTPase, to the many subunits of the *D. discoideum* vacuolar $H^+$-ATPase (p110, p66, p59, p41 and p29) and to a 34 kDa new cysteine protease (Adessi et al., 1995). Whether the polypeptides in the 60-66 kDa molecular mass region could be the CD63 tetraspan requires a control by Western blot analysis with the specific antibodies.

A previous lipid analysis of the vesicles by thin layer chromatography in two dimensions (see FIG. 5 in Tatischeff et al., 1998), indicated the presence of the usual membrane phospholipids (PC, PE, PI, PS) and sphingomyelin. Furthermore, a lysophospholipid, with the characteristic $R_f$ of LBPA was evidenced. Such an analysis takes now its importance, since the lipid analysis of mammalian cell exosomes described LBPA as a specific marker of MVBs and of the derived exosomes (Kobayashi et al., 1998; Kobayashi et al., 2002). It is interesting to recall the observation of the presence of a stereoisomer of LBPA in Dd cells (Ellingson et al., 1980). More recent studies on Dd lysosomes relate the presence of bis(monoacylglycerol) phosphate (BMP) (another name for LBPA), which contributed up to half of the total lipids in lysosomal vacuoles. The presence in an early diverged protist of this lipid characteristic of lysosomes in animal cells, suggested that this phospholipid serves a universal and essential function in endocytosis (Rodriguez-Paris et al., 1993; Nolta et al., 1994). The common presence of LBPA, both in Dd externalised vesicles and in mammalian exosomes, could then suggest an essential function of this lipid in the formation and fusion of vesicles mediating intercellular communication.

In the present study, the fluorescence properties of HO342 were used to demonstrate by spectrofluorimetry that the vesicles externalised from Dd cells grown in presence of HO342 actually contained the dye. That was true for both the <<12,000>> and <<105,000>> vesicles, either purified directly from the cell growth medium (A1), or from the $t_{22}$ starvation medium of the same cells (A2). The fluorescence characteristics of HO342 in buffer A (pH=6.8), as compared to HO342 bound to (Cp) DNA or to lipids, and/or to an anionic detergent, are in general agreement with previous studies on the photophysics of this dye (Gorner et al., 2001; Cosa et al., 2001; Shapiro et al., 1995; Shapiro et al., 1997). Indeed, a bathochromic shift in the dye absorption spectra was observed, as well as a blue-shifted fluorescence emission when HO342 was complexed with DNA. These modifications were associated to an increase in the fluorescence intensity. Such spectral characteristics result from changes in the dipole moment of the molecule upon excitation or decay to the ground state and its interaction with the environment. Due to the structure of the bis-benzimide dye HO342 (FIG. 1a), its fluorescence deactivation is dependent on the configuration of the two benzimidazole units. In aqueous solvent ($\approx$pH 7), the binding between the two benzimidazole units is flexible and a radiationless decay of excitation arises from rotation along the bis-benzimide axis. In contrast, when HO342 is bound to DNA, the shifts in the absorption spectra and in the fluorescence emission, as well as the magnitude of the increase in the fluorescence quantum yield, are dependent on the location of the dye in the DNA structure. HO342 bound in the DNA small groove is only partly protected from the polar environment. Upon excitation, there is a charge transfer process between the two benzimidazole subunits, resulting in a more planar configuration of the molecule. This should be the most predominant conformation in DNA, at a high [bp]/[dye] ratio, due to a rather tight binding of the dye in the DNA groove, which is responsible for the longer-lived component, i.e. for the blue shift and higher intensity of the HO342-DNA complex. However, at the low [bp]/[dye] ratio of our study, the average distance between two dye molecules should be $\approx$1-2 bp, where a steric hindrance could occur, favoring the twisted conformation at the expense of the planar one. The magnitude of the fluorescence increase is therefore lower than at a higher [bp]/[dye] ratio and remains very sensitive to the pH of the environment (Cosa et al., 2001).

The previous studies on the interaction of HO342 with lipids were less spectroscopically documented (Shapiro et al., 1995; Shapiro et al., 1997) than the one with DNA. Some similar mechanism of protection of the hydrophobic part of the dye from the polar environment could explain the observed increase of the HO342 fluorescence intensity, as well as the presence of a blue-shift in the emission maximum, if a planar configuration of the dye is imposed by its interaction with the fatty acyl chains of the lipids. The strong enhancement of fluorescence intensity with a minute blue shift, when HO342 was interacting with the anionic detergent SDS above cmc, could be explained by the partial entry of the dye into the apolar core of the micelles, leading to a less polar environment around at least a part of the benzimidazole rings. The negative charge of SDS at the surface of the micelles probably interacts with the positive charge of the dye, stabilising the configuration of the two rings. Addition of SDS to either HO342-DNA or -lipid complexes which led to a strong red shift towards 470 nm but without a major increase of fluorescence intensity could be explained by a change in the environment around the part of the dye still exposed to the solvent.

This photophysical study allowed giving more detailed information about the state of the dye in Dd vesicles. In the intact vesicles containing HO342, the intensity of the fluorescence emission was about 10 times the maximum of the highest measured concentration of the dye in buffer A (44 μg/ml). This maximum is blue-shifted as with HO342-DNA or -lipid complex. This set of data indicates that the dye within the vesicles is complexed with both DNA and lipids or with only one of these macromolecules, present in or associated with Dd vesicles (Tatischeff et al., 1998). The addition of SDS above cmc clearly disrupts the vesicle membranes, as shown by the decrease in intensity of the second order diffusion peaks. It also increases the HO342 fluorescence intensity by a rather high factor (×25 and ×10 for the A1 and A2 vesicles, respectively), which indicates the presence of free dye inside the vesicles. The presence of free HO342 contained in Dd vesicles agrees with our previous observation of an HO342 fluorescent spot clearly distinct from any of the phospholipids, on the two-dimensional TLC migration of phospholipids extracted from Dd vesicles after HO342 vital staining of the cells (see FIG. 5 in Tatischeff et al., 1998).

Finally, a video light-microscopy study of Dd cells, grown in the absence of HO342 and maintained in presence of the various HO342-containing vesicles, demonstrated the ability of these vesicles to target the DNA specific stain into the nuclei of living Dd cells. A similar study with human leukemic K562 cells, either sensitive (s) or multidrug resistant (r), evidenced the capacity of the Dd HO342-containing vesicles to transfer the dye into the nuclei of the human cells, as well. The efficient targeting of HO342 to the nuclei of living cells is then to be ascribed to the Dd vesicle-mediated delivery of free HO342. It is to be noticed that, in these conditions, only the nuclei of the cells appeared stained and not the membrane or any other cell compartment, i.e. the well-acknowledged specificity of HO342 for DNA was maintained at the cell level.

Difference between the two types of vesicles isolated from Dd cell growth medium, <<12,000>> and <<105,000>> A1, has been observed in the present report. If both types are able to transfer the dye to cell nuclei, the time required for an efficient staining of the nuclei inside Dd cells was $\approx$7 times longer with the <<105,000>> A1 vesicles than with the <<12,000>> A1 vesicles. The rather long time ($\approx$3 h30) necessary for a full staining of Dd nuclei inside Dd cells with the <<105,000>> vesicles was comparable to the one necessary for nuclei staining inside K562r cells in the same conditions. With regard to the simultaneous HO342 transfer to nuclei of K562r and K562s cells mediated by <<12,000>> A1 vesicles, after overnight incubation, it is to be noticed that the efficiency of staining seemed comparable for both cell types. It is noteworthy that after such a long incubation time without proper oxygenation, the observed K562 cells were not lysed, suggesting a protective influence of the Dd vesicles on the human cell membranes. However, compared with the shorter incubation time used with the <<105,000>> vesicles, most of the stained nuclei seemed to occupy the full K562 cells, suggesting a possible pre-apoptotic decrease in size after overnight incubation.

The efficiency of transfer of HO342 mediated by <<12,000>> and <<105,000>> A2 vesicles isolated from the $t_{22}$ starvation medium was compared simultaneously on the three cell types with overnight incubation. The nuclei of K562s cells were much more stained with the <<12,000>> A2 vesicles than with the <<105,000>> A2 vesicles. The nuclei of K562r cells were stained by the <<12,000>> A2 vesicles with a much lower efficiency than the nuclei of K562s cells. Staining of the K562r nuclei with the <<105,000>> A2 vesicles was very faint. Dd cells were also more efficiently stained with the <<12,000>>A2 vesicles than with the <<105,000>> A2 vesicles.

The unicellular apoptotic death of Dd cells induced by starvation in a $t_{22}$ conditioned buffer has been described previously (Tatischeff et al., 2001). Presently by starving Dd cells, in the $t_{22}$ starvation medium used for purifying the A2 vesicles, an induced-apoptotic death was observed by morphologic criteria. However, starvation of Dd cells in the same 105,000 g clarified supernatant, which was depleted of all A2 vesicles, did not induce cell death (data not shown). This suggests a leading role of the A2 vesicles in the induction of apoptotic Dd cell death.

The externalisation of vesicles may be a general property of many cell types, first mentioned in 1981 (Trams et al., 1981). However, there seems to be an important heterogeneity in origin, nature, protein composition and physiological functions—mostly yet unknown—of the described extracellular vesicles. Two types of membrane vesicles were released from activated platelets and discriminated by their size: microvesicles (100 nm to 1 μm in diameter) were externalised by surface shedding and exosomes (40-100 nm in diameter) were secreted after fusion of MVBs with the plasma membranes (Heijnen et al., 1999). During apoptotic cell death, cells are also blebbing and expelling apoptotic bodies of different sizes, which are mixed with the other externalised vesicles (Thery et al., 2001).

Therefore, new cells are always "bathed" with a lot of vesicles expelled from ancester cells, which represents a kind of cell <<memory>> with all the prints of the previous cell life. Potentially, it is a general source of intercellular communication, which is only beginning to be unravelled. Most works have been focused on the smallest vesicles, called exosomes (Thery et al., 2002; Stoorvogel et al., 2002), which can stimulate the immune system through signal transmission to cells of the hematopoietic lineage (Denzer et al., 2000a; Blanchard et al., 2002; Thery et al., 2002; Thery et al., 2001, Stoorvogel et al., 2002, Denzer et al., 2000b; Skokos et al., 2001). Vesicles externalised by tumour cells can also be used for tumour detection (Bergsmedh et al., 2001; Anker et al., 2003), or for immunisation against tumours (Wolfers et al., 2001; Andre et al., 2002).

The present report corroborate inventors' previous studies on Dd externalised vesicles (Tatischeff et al., 1998; Tatischeff et al., 2001), and whatever their origin from the cell organelles, probably differing in relation with their size heterogeneity (57-500 nm), they are the end-point of a very efficient membrane traffic inside Dd cells (Rodriguez-Paris et al., 1993; Nolta et al., 1994; Adessi et al., 1995; Aguado-Velasco et al., 1999; Neuhaus et al., 2002; Seastone et al., 2001). Their externalisation and their ability to communicate information to the other cells indicate that this early diverged protist could be used as a valuable model for helping to clarify the complexity of the yet largely unknown vesicle-mediated intercellular communications.

Dd cells were known to be as motile as leukocytes and as efficient for phagocytosis as macrophages. The intensive membrane traffic displayed by these non pathogenic amoebae shows also amazing similarities with membrane traffic of mammalian cells.

The process of vesicle externalisation shared by Dd cells with many human cells thus appears to provide an important mean of intercellular communication. It is interesting to remark that such a role was efficient enough to survive through evolution since about 1 billion years. Due to this outstanding conservation of many essential functions from Dd to human, Dd vesicles thus provide useful drug vectors for targeting human cells, optionally associated with a very specific targeting of the intracellular goal. Efficient drug targeted delivery inside pathological cells is indeed a general problem, encountered both in the treatment of resistant tumours and for efficiently applying antigene or antisense therapy.

Example 9

Internalisation of an Exogenous Molecule and its Release in Vesicles is a General Process in *D. discoideum* Cells The capacity of Dd cells to internalise different exogenous molecules was studied. Further, their ability to release vesicles, in particular the "12,000" vesicles, carrying a broad-spectrum of molecules of interest was assessed. Flow cytometry and micro-spectrofluorimetry were used to measure respectively the cell internalisation and the vesicle-mediated release of the fluorescent cargo molecule as a function of incubation time in the growth medium. Growing Dd cells were incubated for different periods of time up to 72 h in the presence of the exogenous molecule. Fractions of the cells were fixed in 2% paraformaldehyde after each one of these increasing incubation times. Simultaneously, the externalised "12,000" vesicles were prepared from aliquots of the growth medium and concentrated (×20). As controls, Dd cells were grown in parallel without the cargo molecule and handled the same. Moreover, cell counting during growth allowed to check for any cytotoxicity of the studied molecule as a function of time. Cell and vesicle samples were kept at 4° C. until measurements.

Different molecules of potential therapeutic interest were studied as cargo:

a) Hypericin

In the presence of hypericin (25 μM), an extremely hydrophobic molecule proposed for antitumoral dynamic phototherapy, Dd cells were rapidly stained without any apparent toxicity. After a 4 h-incubation, the stained cells had released but very few vesicles into their growth medium. After a 24 h-incubation, the cells had lost part of their hypericin content, whereas a significant amount of hypericin-loaded vesicles was collected. After a 48 h-incubation, the cells had lost most of their staining and hypericin was found associated with the high amount of vesicles released into the growth medium. The endogenous red-fluorescent molecule protoporphyrin PPIX, already evidenced in Dd vesicles (Arnoult et al, 2001), was followed by its characteristic emission spectrum in the hypericin-containing vesicles as well as in the control vesicles.

b) Doxorubicine (also called Adriamycine)

This compound belongs to the anthracyclin family widely used in antitumoral chemotherapy. The study showed that this red-emitting molecule is also released into "12,000" vesicles. Accordingly, Dd vesicles carrying one of the numerous related anthracyclin compounds of quite different hydrophobicity makes it possible to address the question of the influence of hydrophobicity on the efficiency of the anthracyclin transfer into leukemic human cells expressing multidrug resistance against antitumoral chemotherapy.

c) Fluorescein-Labelled Oligodeoxynucleofide (ODN)

To assess whether Dd vesicles could be used as a support for gene therapy, it was checked whether a fluorescent ODN, already used as a control for multidrug resistance (mdr) silencing, could also be carried by Dd vesicles. It was found that, contrary to similar experiments with mammalian cells, this ODN did penetrate into Dd cells and escaped rapid nuclease degradation.

d) Reporter Plasmid (Peroxidase or GFP).

Experiments to check whether Dd vesicles might transport high-sized (about 2.5 to 5 kb) DNA plasmids are conducted with a fluorescently labelled plasmid, in order to follow Dd cell internalisation and vesicle-mediated externalisation.

Altogether, these results demonstrate that internalisation of an exogenous molecule into *Dictyostelium* cells followed by its vesicle-mediated release from the cells is a general process, whatever the nature of the exogenous molecule.

REFERENCES

Adessi C., Chapel A., Vincon M., Rabilloud T., Klein G., Satre M., Garin J. (1995) Identification of major proteins associated with *Dictyostelium discoideum* endocytic vesicles. J. Cell Sci. 108: 3331-3337

Aguado-Velasco C, Bretscher M S. (1999) Circulation of the plasma membrane in *Dictyostelium*. Mol. Biol. Cell 10: 4419-4427

Andre F., Schartz N. E., Movassagh M., Flament C., Pautier P., Morice P., et al. (2002) Malignant effusions and immunogenic tumour-derived exosomes. Lancet 360: 295-305

Anker P, Mulcahy H, Stroun M. (2003) Circulating nucleic acids in plasma and serum as a noninvasive investigation for cancer: time for large-scale clinical studies? Int. J. Cancer 103:149-152

Asahi K, Sakurai A, Takahashi N, Kubohara Y, Okamoto K, Tanaka Y (1995) DIF-1, morphogen of *Dictyostelium discoideum*, induces the erythroid differentiation in murine and human leukemia cells. Biochem Biophys Res Commun.; 208:1036-9

Bergsmedh A., Szeles A., Henriksson M., Bratt A., Folkman M. J., Spetz A. L., Holmgren L. (2001) Horizontal transfer of oncogenes by uptake of apoptotic bodies. Proc. Natl. Acad. Sci. U S A 98: 6407-6411

Blanchard N., Lankar D., Faure F., Regnault A., Dumont C., Raposo G., Hivroz C. (2002) TCR activation of human T cells induces the production of exosomes bearing the TCR/CD3/Z complex. J. Immunology 168: 3235-3241

Cosa G., Focsaneanu K. S., McLean J. R., McNamee J. P. and Scaiano, J. C. (2001) Photophysical properties of fluorescent DNA-dyes bound to single- and double-stranded DNA in aqueous buffered solution. Photochem. Photobiol. 73: 585-599

Denzer K., Kleijmeer M. J., Heijnen H. F., Stoorvogel W. and Geuze H. J. (2000a) Exosome: from internal vesicle of the multivesicular body to intercellular signaling device. J. Cell Sci. 113: 3365-3374

Denzer K., van Eijk M., Kleijmeer M. J., Jakobson E., de Groot C., Geuze H. J. (2000b) Follicular dendritic cells carry MHC class II-expressing microvesicles at their surface. J. Immunol. 165:1259-1265

Ellingson J. (1980) Identification of N-acylethanolamine phosphoglycerides and acylphosphatidylglycerol as the phospholipids which disappear as *Dictyostelium discoideum* cells aggegate. Biochemistry 19: 6176-6182

Gorner H. (2001) Direct and sensitized photoprocesses of bis-benzimidazole dyes and the effects of surfactants and DNA. Photochem. Photobiol. 73: 339-348

Heijnen H. F., Schiel A. E., Fijnheer R., Geuze H. J., Sixma J. J. (1999) Activated platelets release two types of membrane vesicles: microvesicles by surface shedding and exosomes derived from exocytosis of multivesicular bodies and alpha-granules. Blood 94: 3791-3799

Izquierdo M. A., Scheffer G. L., Flens M. J., Giaccone G., Broxterman H. J., Meijer C. J., van der Valk P., Scheper R. J. (1996) Broad distribution of the multidrug resistance-related vault lung resistance protein in normal human tissues and tumors. Am. J. Pathol. 148: 877-887

Klein R. and Tatischeff 1. (1987) Tautomerism and fluorescence of lumazine. Photochem. Photobiol. 45: 55-65

Kobayashi T., Stang E., Fang K. S., de Moerloose P., Parton R. G. and Gruenberg J. (1998) A lipid associated with the antiphospholipid syndrome regulates endosome structure and function. Nature 392, 193-197

Kobayashi T., Beuchat M. H., Chevallier J., Makino A., Mayran N., Escola J. M., et al. (2002) Separation and characterization of late endosomal membrane domains. J. Biol. Chem. 277: 32157-32164

Laemmli U. K. (1970) Cleavage of structural proteins during the assembly of the head of bacteriophage T4. Nature 227: 680-685

Loetchutinat C., Saengkhae C., Marbeuf-Gueye C., and Gamier-Suillerot A. (2003) New insights into the P-glycoprotein-mediated effluxes of rhodamines. Eur. J. Biochem. 270: 476-485

Melton D., ed. (1988) Antisense DNA and RNA, (Cold Spring Harbor Laboratory)

Morris H R, Taylor G W, Masento M S, Jermyn K A, Kay R R. (1987) Chemical structure of the morphogen differentiation inducing factor from *Dictyostelium discoideum*. Nature 328:811-4

Neuhaus E. M., Almers W., Soldati T. (2002) Morphology and dynamics of the endocytic pathway in *Dictyostelium discoideum*. Mol. Biol. Cell 13:1390-1407

Nolta K. V., Rodriguez-Paris J. M., Steck T. L. (1994) Analysis of successive endocytic compartments isolated from *Dictyostelium discoideum* by magnetic fractionation. Biochim. Biophys. Acta 1224: 237-246

Olson F., Hunt C. A., Szoka F. C., Vail W. J. and Papahadjopoulos D. (1979) Preparation of liposomes of defined size distribution by extrusion through polycarbonate membranes. Biochim. Biophys. Acta 557: 9-23

Peterson G. L. (1977) A simplification of the protein assay method of Lowry et al. which is more generally applicable. Anal. Biochem. 83: 346-356

Poppenborg L, Friehs K, Flaschel E. (1997) The green fluorescent protein is a versatile reporter for bioprocess monitoring. J. Biotechnol. 1997 58:79-88

Rodriguez-Paris J. M., Nolta K. V., Steck T. L. (1993) Characterization of lysosomes isolated from *Dictyostelium discoideum* by magnetic fractionation. J. Biol. Chem. 268: 9110-9116

Seastone D. J., Harris E., Temesvari L. A., Bear J. E., Saxe C. L., Cardelli J. (2001) The WASp-like protein Scar regulates macropinocytosis, phagocytosis and endosomal membrane flow in *Dictyostelium*. J. Cell Sci. 114: 2673-2683

Shapiro A., Corder A. and Ling V. (1997) P-Glycoprotein-mediated Hoechst 33342 transport out of the lipid bilayer. Eur. J. Biochem. 250: 115-121

Shapiro, A. B. and Ling, V. (1995) Reconstitution of drug transport by purified P-glycoprotein. J. Biol. Chem. 270: 16167-16175

Sharp P A. (2001) RNA interference–2001 *Genes Dev* 15, 485-490.

Skokos D., Le Panse S., Villa I., Rousselle J. C., Peronet R., David B., et al. (2001) Mast cell-dependent B and T lymphocyte activation is mediated by the secretion of immunologically active exosomes. J. Immunol. 166: 868-876

Sussman M. (1987) Cultivation and synchronous morphogenesis of *Dictyostelium* under controlled experimental conditions. In: *Dictyostelium discoideum*: Molecular Approaches to Cell Biology, Methods Cell Biol. vol. 28, pp. 9-29, Spudich J. A. (ed.), Academic Press, Inc.

Stoorvogel W., Kleijmeer M. J., Geuze H. J., Raposo G. (2002). The biogenesis and functions of exosomes. Traffic. 3: 321-330

Tatischeff I., Bomsel M., de Paillerets C., Durand H, Geny B., Segretain D., Turpin E. and Alfsen A. (1998) *Dictyostelium discoideum* cells shed vesicles with associated DNA and vital stain Hoechst 33342. Cell. Mol. Life Sci. 54: 476-487

Tatischeff I., Petit P. X., Grodet A., Tissier J. P., Duband-Goulet I. and Ameisen J. C. (2001) Inhibition of multicellular development switches cell death of *Dictyostelium discoideum* towards mammalian-like unicellular apoptosis. Eur. J. Cell Biol. 80: 428-441

Thery C., Boussac M., Veron P., Ricciardi-Castagnoli P., Raposo G., Garin J., Amigorena S. (2001) Proteomic analysis of dendritic cell-derived exosomes: a secreted subcellular compartment distinct from apoptotic vesicles. J Immunol. 166: 7309-7318

Thery C., Zitvogel L., Amigorena S. (2002) Exosomes: composition, biogenesis and function. Nat. Rev. Immunol. 2: 569-579

Trams E. G., Lauter C. J., Salem N., Heine U. (1981) Exfoliation of membrane ecto-enzymes in the form of microvesicles. Biochim. Biophys. Acta. 645: 63-70

Watts D. J. and Ashworth J. M. (1970) Growth of myxamoebae of the cellular slime mould *Dictyostelium* in axenic culture. Biochem. J. 119: 171-174

Wolfers J., Lozier A., Raposo G., Regnault A., Thery C., Masurier C., et al. (2001) Tumor-derived exosomes are a source of shared tumor rejection antigens for CTL cross-priming. Nat. Med. 7: 297-303

The invention claimed is:

1. A method for preparing a non-pathogenic amoeba vesicle for delivering a molecule of interest to an eukaryotic target cell, which method comprises the steps consisting of:
   a) culturing a non-pathogenic amoeba cell in a culture medium comprising said molecule of interest, under conditions sufficient to allow the non-pathogenic amoeba cell to release vesicles; and
   b) recovering a vesicle released by said non-pathogenic amoeba cell, which vesicle contains said molecule of interest,
   wherein said molecule of interest is selected from the group consisting of a therapeutic molecule, an imaging agent and a diagnostic agent, with the proviso that said vesicle is not a Hoechst 33342-containing *Dictyostelium discoideum* vesicle.

2. The method according to claim 1, wherein said non-pathogenic amoeba is *Dictyostelium discoideum*.

3. The method of claim 1, wherein said molecule of interest is a therapeutic molecule.

4. The method of claim 1,
   wherein said therapeutic molecule is selected from the group consisting of an antibiotic, an antimicrobial agent, an antimycobacterial, antifungal, or antiviral agent, an agent affecting the immune response, a blood calcium regulator, an agent useful in glucose regulation, an anticoagulant, an antithrombotic, an antihyperlipidemic agent, a cardiac drug, a thyromimetic or antithyroid drug, an adrenergic, an antihypertensive agents, a cholinergic, an anticholinergic, an antispasmodic, an anti-ulcer agent, a skeletal and smooth muscle relaxant, a prostaglandin, a general inhibitor of the allergic response, an antihistamine, a local anesthetic, an analgesic, a narcotic antagonist, an antitussive, a sedative-hypnotic agent, an anticonvulsant, an antipsychotic, an anti-anxiety agent, an antidepressant agent, an anorexigenic, a non-steroidal anti-inflammatory agent, a steroidal anti-inflammatory agent, an antioxidant, a vasoactive agent, a bone-active agent, an anti-arthritic agent and an anti-neoplastic agent.

5. The method of claim 1, wherein said therapeutic molecule is an anti-neoplastic agent.

6. The method of claim 1, wherein said therapeutic molecule is an antibiotic.

7. The method of claim 1, wherein said molecule of interest is an imaging agent.

8. The method of claim 1, wherein said molecule of interest is a diagnostic agent.

9. The method of claim 1, wherein said molecule of interest is selected from the group consisting of a small chemical molecule, a small organic or inorganic compound and a nucleic acid.

10. The method of claim 1, wherein said target cell is a human cell.

11. The method of claim 1, wherein said molecule of interest is not Hoechst 33342.

12. The method of claim 2, wherein said molecule of interest is a therapeutic molecule.

13. The method of claim 2,
   wherein said therapeutic molecule is selected from the group consisting of an antibiotic, an antimicrobial agent, an antimycobacterial, antifungal, or antiviral agent, an agent affecting the immune response, a blood calcium regulator, an agent useful in glucose regulation, an anticoagulant, an antithrombotic, an antihyperlipidemic agent, a cardiac drug, a thyromimetic or antithyroid drug, an adrenergic, an antihypertensive agents, a cholinergic, an anticholinergic, an antispasmodic, an anti-ulcer agent, a skeletal and smooth muscle relaxant, a prostaglandin, a general inhibitor of the allergic response, an antihistamine, a local anesthetic, an analgesic, a narcotic antagonist, an antitussive, a sedative-hypnotic agent, an anticonvulsant, an antipsychotic, an anti-anxiety agent, an antidepressant agent, an anorexigenic, a nonsteroidal anti-inflammatory agent, a steroidal anti-inflammatory agent, an antioxidant, a vasoactive agent, a bone-active agent, an anti-arthritic agent and an anti-neoplastic agent.

14. The method of claim 2, wherein said therapeutic molecule is an anti-neoplastic agent.

15. The method of claim 2, wherein said therapeutic molecule is an antibiotic.

16. The method of claim 2, wherein said molecule of interest is an imaging agent.

17. The method of claim 2, wherein said molecule of interest is a diagnostic agent.

18. The method of claim 2, wherein said molecule of interest is selected from the group consisting of a small chemical molecule, a small organic or inorganic compound and a nucleic acid.

19. The method of claim 2, wherein said target cell is a human cell.

20. An isolated non-pathogenic amoeba vesicle for delivering a molecule of interest to an eukaryotic target cell, wherein said vesicle contains a molecule of interest selected from the group consisting of a therapeutic molecule, an imaging agent and a diagnostic agent, with the proviso that said vesicle is not a Hoechst 33342-containing *Dictyostelium discoideum* vesicle.

21. The vesicle according to claim 20, wherein said non-pathogenic amoeba is *Dictyostelium discoideum*.

22. The isolated non-pathogenic amoeba vesicle of claim 20, wherein said molecule of interest is a therapeutic molecule.

23. The isolated non-pathogenic amoeba vesicle of claim 20, wherein said molecule of interest is an imaging agent.

24. The isolated non-pathogenic amoeba vesicle of claim 20, wherein said molecule of interest is a diagnostic agent.

25. The isolated non-pathogenic amoeba vesicle of claim 20, wherein said molecule of interest is selected from the group consisting of a small chemical molecule, a small organic or inorganic compound, and a nucleic acid.

26. The isolated non-pathogenic amoeba vesicle of claim 20, wherein said target cell is a human cell.

27. The isolated non-pathogenic amoeba vesicle of claim 20, wherein said molecule of interest is not Hoechst 33342.

28. The isolated non-pathogenic amoeba vesicle of claim 21, wherein said molecule of interest is a therapeutic molecule.

29. The isolated non-pathogenic amoeba vesicle of claim 21, wherein said molecule of interest is an imaging agent.

30. The isolated non-pathogenic amoeba vesicle of claim 21, wherein said molecule of interest is a diagnostic agent.

31. The isolated non-pathogenic amoeba vesicle of claim 21, wherein said molecule of interest is selected from the group consisting of a small chemical molecule, a small organic or inorganic compound, and a nucleic acid.

32. The isolated non-pathogenic amoeba vesicle of claim 21, wherein said target cell is a human cell.

* * * * *